United States Patent [19]

Panzer et al.

[11] 4,108,883

[45] Aug. 22, 1978

[54] PROPIONIMIDATE HYDROHALIDES

[75] Inventors: Hans Peter Panzer, Stamford; Michael Niall Desmond O'Connor, Norwalk; Louis J. Baccei, Newington, all of Conn.

[73] Assignee: American Cyanamid Company, Stamford, Conn.

[21] Appl. No.: 752,497

[22] Filed: Dec. 20, 1976

Related U.S. Application Data

[62] Division of Ser. No. 706,086, Jul. 16, 1976, Pat. No. 4,044,009, which is a division of Ser. No. 467,332, May 6, 1974, Pat. No. 4,007,200.

[51] Int. Cl.$^2$ .......................................... C07C 119/18
[52] U.S. Cl. ............................................. 260/453 RW
[58] Field of Search ................................ 260/453 RW

[56] References Cited

U.S. PATENT DOCUMENTS

| 2,091,257 | 8/1937 | Eckelmann et al. | 260/453 RW |
|---|---|---|---|
| 2,553,564 | 5/1951 | Fein et al. | 260/453 RW |
| 3,166,588 | 1/1965 | Johnson | 260/453 RW |

Primary Examiner—Lewis Gotts
Assistant Examiner—Robert C. Whittenbaugh

Attorney, Agent, or Firm—Frank M. Van Riet

[57] ABSTRACT

Compounds having the formulae

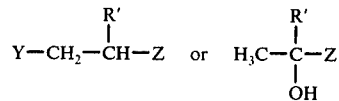

wherein Y is hydroxyl or $R^2O$, wherein $R^2$ is alkyl, aryl or aralkyl, R' is hydrogen, methyl or phenyl and Z is

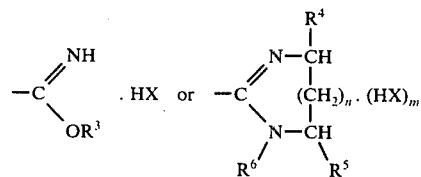

wherein $n$ and $m$ are, individually, 0 or 1, X is a halogen, $R^3$ is alkyl, hydroxyalkyl, or alkoxyalkyl and $R^4$, $R^5$ and $R^6$ are, individually, hydrogen, alkyl, aryl, alkaryl or aralkyl, and methods for their production, are disclosed.

6 Claims, No Drawings

PROPIONIMIDATE HYDROHALIDES

This is a division, of application Ser. No. 706,086, filed July 16, 1976, now U.S. Pat. No. 4,044,009 which, in turn, is a division of application Ser. No. 467,332, filed May 6, 1974, now U.S. Pat. No. 4,007,200.

BACKGROUND OF THE INVENTION

The market for high-efficiency products for use in the treatment of aqueous suspensions of particulate, solid, water-insoluble materials has become increasing acute in recent years. Industry and research are therefore continually searching for new systems which can be used to facilitate the dewatering of aqueous suspensions of organic, or mixtures of organic and inorganic, materials such as distillary wastes, fermentation wastes, wastes from paper manufacturing plants, dye plant wastes and sewage suspensions such as digested sludges, activated sludges or raw and primary sludges from sewage treatment plants etc.

The most recent and most successful materials used in the treatment of such suspensions have been amidine or, imidazoline polymers, see U.S. Pat. Nos. 3,406,139; 3,666,705; 3,450,646; 3,576,740. These polymers are very effective materials for use in the treatment of industrial wastes. The polymers are produced, however, by the treatment of corresponding nitrile polymers and are therefore governed in their structure by the structure of the nitrile polymers. Furthermore, conversion of the nitrile polymers to the imidazoline or amidine polymers does not reach 100% and therefore a portion of the resultant imidazoline or amidine polymer is nonfunctional in its water treating capacity.

Prior attempts to obviate these difficulties have included rearrangement of the groups present in the nitrile charge polymer and the attempted production of unsaturated imidazolines which may be homopolymerized or copolymerized into more active imidazoline polymers. However, attempts to produce intermediates, from which the unsaturated imidazolines may be prepared, have proven unsuccessful. Furthermore, attempts to follow the teachings of U.S. Pat. No. 3,210,371 resulted only in the production of polymers while the teachings of Oxley et al, Jour. Chem. Soc., 1947, pages 497–503 also resulted in the recovery of polymeric products.

SUMMARY

We have now succeeded in the production of a novel class of intermediates which can be used to manufacture unsaturated imidazoline monomers which, in turn, can be homopolymerized and copolymerized into polymers useful in the treatment of water sludges, the formation of fibers and the treatment of paper etc.

DESCRIPTION OF THE INVENTION INCLUDING PREFERRED EMBODIMENTS

The novel compounds of the present invention have the formulae

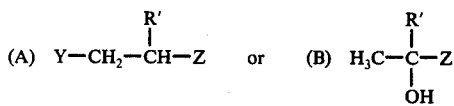

wherein Y is hydroxyl or $R^2O$, wherein $R^2$ is alkyl $(C_1-C_{10})$, aryl $(C_6-C_{10})$ or aralkyl $(C_7-C_{11})$, R' is hydrogen, methyl or phenyl and Z is

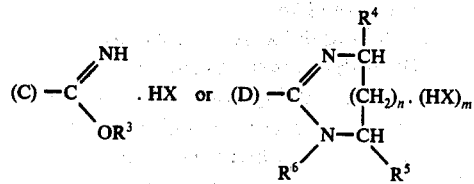

wherein $n$ and $m$, are, individually, 0 or 1, X is a halogen, $R^3$ is alkyl $(C_1-C_4)$, hydroxyalkyl $(C_2-C_4)$ or alkoxyalkyl $(C_2-C_4)$ and $R^4$, $R^5$ and $R^6$ are, individually, hydrogen, alkyl $(C_1-C_4)$, aryl $(C_6-C_{10})$, aralkyl $(C_7-C_{11})$ or alkaryl $(C_7-C_{11})$.

The compounds of Formula (C) are prepared by the Pinner reaction according to either of the equations:

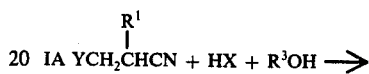

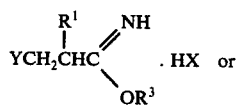

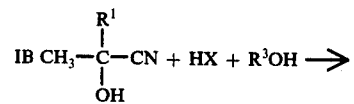

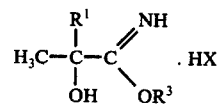

Y, R', $R^2$, $R^3$ and X being as described above.

The reactants are utilized in concentrations such that from about equimolar amounts up to an excess of about 10% of the acid per mole of cyano compound and from about equimolar amounts up to a slight excess of the hydroxy (alcohol) compound per mole of the cyano compound are employed.

The reaction is conducted at a temperature ranging from about $-20°$ C. to about 30° C., preferably from about $-15°$ C. to about 15° C. This temperature range has been found to be successful in preventing extensive side reaction between the acid and the alcohol charges. The pressure of the reaction zone should be maintained at atmospheric but subatmospheric or superatmospheric pressures may be used, if desired or necessary.

The reaction is allowed to proceed for from about 2 to about 72 hours, preferably from about 12 to about 36 hours, in the absence of any catalytic material. The use of a catalyst is not precluded, however. The reaction must be conducted under anhydrous conditions in the presence of an anhydrous solvent. Sufficient solvent to dissolve the charge ingredients is all that is required. Xylene, toluene, benzene, methylene chloride, petroleum ether, ether, dioxane, tetrahydrofuran, aliphatic hydrocarbons and the like have been found useful. Also the alcohol ($R^3OH$) may be used as a solvent.

Examples of useful cyano starting compounds in Equations IA and IB include β-methoxypropionitrile, β-ethoxypropionitrile, β-butoxypropionitrile, β-octyloxypropionitrile, β-naphthyloxypropionitrile, β-dicycloxypropionitrile, β-phenoxypropionitrile, α-methyl-β-methoxypropionitrile, α-methyl-β-propoxypropionitrile, α-methyl-β-hexoxypropionitrile, acetone cyanohydrin, ethylene cyanohydrin, acetophenone cyanohydrin, and the like.

The alcohols useful as starting materials in Equations IA and IB in the present invention include methanol, ethanol, 1-or 2-hydroxypropane, 1- or 2-hydroxybutane, 1,3-dihydroxybutane, 1,2-dihydroxypropane, 1,4-dihydroxybutane, 1,3-dihydroxybutane, 1,2-dihydroxypropane, methoxymethanol, ethoxymethanol, methoxyethanol, 1-methoxy-2-propanol, and the like.

The acidic compounds include hydrochloric acid, hydrofluoric acid, hydrobromic acid and hydroiodic acid.

These compounds of Formula (C) are crystalline and are used to prepare the compounds of Formula (D).

The compounds of Formula (D) wherein $m=0$ are produced according to the equations:

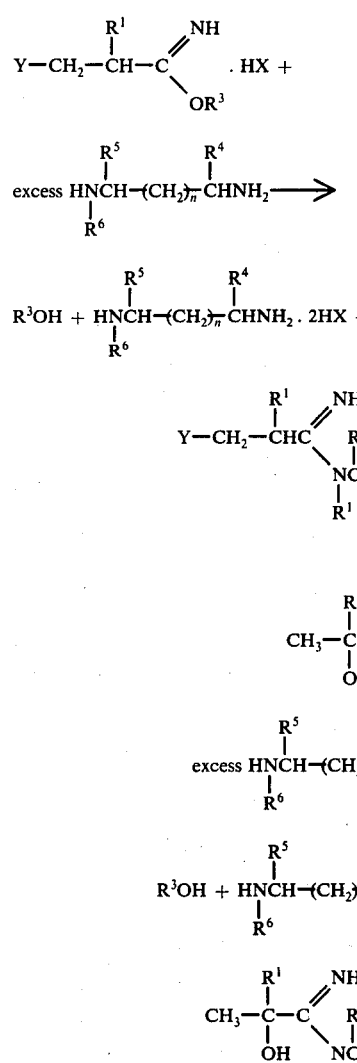

and

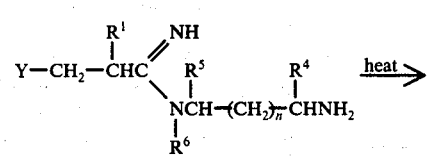

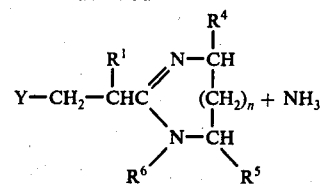

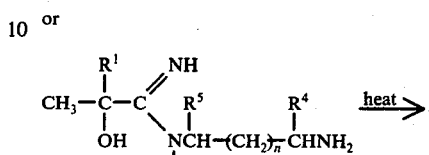

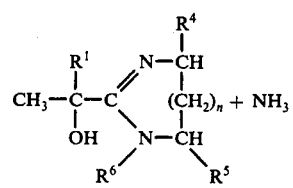

The compounds of Formula (D) wherein $m=1$ are produced according to the equations:

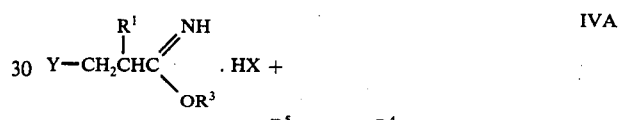

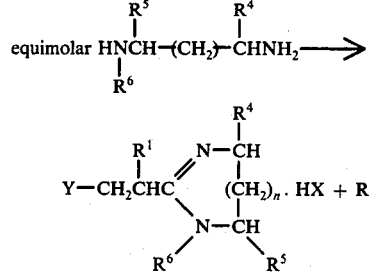

or

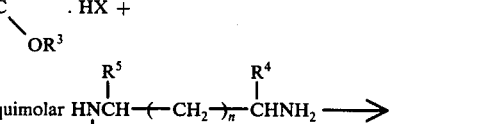

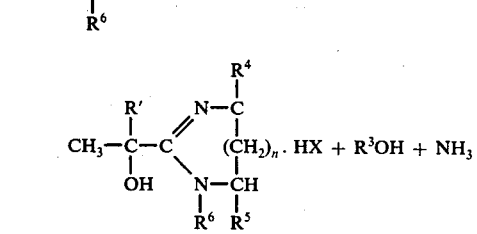

wherein Y, R', X, $R^3$, $R^4$, $R^5$, $R^6$ and $n$ are as described above.

The reactions of equations IIA and IIB are conducted utilizing at least about an 0.5 mole excess of the diamine per mole of HX in the compound (C) charge.

The entire reaction media resulting from the Equation IA or IB reactions may be used as a charge to the Equation IIA or IIB reactions or Compound (C) may be isolated, such as by filtration, and used per se as the charge in the production of Compound (D) where m=0. The IIA and IIB reactions are conducted by adding the excess diamine at the temperature of the reaction mediae resulting from the Equation IA or IB reactions, with stirring and allowing the resultant media to warm to room temperature over a period of from about 1 to about 24 hours. The reactions are conducted at atmospheric pressure in the presence of the same solvents as mentioned above, the diamine being added as a solution therein. No catalyst need be employed but the conditions must be kept anhydrous, as above.

After the reaction media has reached ambient temperature, the diamine HX crystals are removed by filtration, centrifugation etc. If desired, the excess diamine mentioned above may be replaced by an additional scavenger such as a tertiary amine, e.g. triethylamine. In this instance, the diamine reacts only with the Compound (C) charge and the secondary scavenger picks up the HX released. Other suitable scavengers include suitable ion exchangers such as that sold as Amberlyst A21. These secondary scavengers are removed from the reaction media by filtration etc.

The resultant materials are then used per se without product isolation as the charges to Equations IIIA and IIIB. Compound (D), where m=0, is produced by heating either charge to about 20° C., but below about 150° C., i.e. below the boiling point of the solvent, while bubbling nitrogen gas into the reaction media. This procedure results in the production of a solvent solution of Compound (D) which is then usually in the presence of a slight amount of salt or other impurity which, when heated, cause the Compound (D) product to resinify (polymerize). This resinification can be prevented by either of two techniques which comprise:

1. Adding an aqueous solution of caustic, which is preferably cold i.e. at about 5° C., shaking the resultant media, allowing the media to settle into two phases, discarding the water phase, drying the solvent phase and distilling off the solvent, or
2. Running the Compound (D) solution through an ion-exchanger which is solvent pretreated with the same solvent in the reaction media and is preferably macro-reticular. Suitable ion-exchangers include those mentioned above.

When preparing Compound (D) where m=1, the charge ingredients are the same as those described above for when m=0, however, an excess of the diamine is not employed, nor is any scavenger. As a result, all the diamine reacts with the imidoester and the HX salt portion of the compound remains as such. Treatment of the Compound (D) HX salt, as described above for resinification prevention with regard to Compound (D) when m=0, results in the removal of the HX portion of the compound and recovery of the Compound (D), m=0, product.

The compounds of Formula (D), where m=0 or 1, are also crystalline solids or high boiling liquids.

Examples of suitable diamines which may be used in the Equation IIA, IIB, IVA and IVB reactions include ethylene diamine, propylene diamine, N,N¹-dimethylpropylene diamine as well as those set forth at column 4, line 60 to column 5, line 2 of U.S. Pat. No. 3,406,139, which patent is hereby incorporated herein by reference.

The compounds of Formula (D) find use primarily in the production of their ethylenically unsaturated derivatives, which derivatives may be formed into useful polymers. The unsaturated derivatives are prepared as set forth in our copending application, Ser. No. (Case No. 25,206), filed concurrently herewith, and entitled UNSATURATED IMIDAZOLINES, which application is hereby incorporated herein by reference, The following examples are set forth for purposes of illustration only and are not to be construed as limitations on the present invention except as set forth in the appended claims. All parts and percentages are by weight unless otherwise specified.

EXAMPLE 1

(Part A)

To a 3-necked reaction vessel equipped with stirrer, gas delivery tube, thermometer and reflux condenser is charged 85.1 parts of 3-methoxypropionitrile, 32.0 parts of reagent grade methanol and 300 parts of toluene. The exit from the reflux condenser is connected to a drying tower filled with a commercially available drying agent and a bath is provided for cooling the vessel below 0° C. Hydrochloric acid gas flow is controlled by means of a rotameter and is passed through a calcium chloride filled trap which serves both as a means for drying the gas and as a receiver in case liquid is sucked back into the line. After charging the reagents and toluene, the solution is stirred and cooled to 3° C. and the HCl gas is then fed, while controlling the temperature to −4° to 1° C., until 38.0 parts have been added. The HCl gas is added as rapidly as possible commensurate with complete adsorption and good temperature control. The mixture is then stirred for 15 hours in an ice bath (maximum 10° C.). Crystals of methyl-3-methoxypropionimidate hydrochloride appear 2.25 hours after the HCl addition is complete. 46.5 Hours after the HCl addition is stopped, an 80% yield of methyl-3-methoxypropionimidate hydrochloride is formed.

(Part B)

400 Parts of toluene are then added to the reaction media resulting from Part A at −5° C. over a period of 8 minutes. The solution is cooled to −8° C. and 95.25 parts (molar excess) of dry ethylenediamine, dissolved in 250 parts of toluene, are added while controlling the temperature to −7° C. to 3° C. The first half of the ethylenediamine is added dropwise due to the extreme exothermic reaction which takes place. The entire amount of ethylenediamine is added in 17 minutes. The resultant reaction mixture is stirred and warmed to 20° C. over 15 L hours. Higher temperatures (>20° C.) result in a mixture of hydrochlorides being formed and a corresponding reduction in yield of the desired product.

The ethylenediamine dihydrochloride which forms is then filtered off and washed three times with toluene. The combined filtrate and washings are then heated to 47°–57° C. while bubbling nitrogen gas slowly through the vessel until the evolution of ammonia ceases (5 hours) after removing the calcium chloride drying tower. Care is used to prevent the temperature from rising above 60° C. since side reactions cause the formation of resinous material.

The resultant solution is then cooled to 5° C. and 100 parts of a cold (5° C.) 30% sodium hydroxide solution are added to extract any hydrochloric acid remaining. Two phases form, the lower aqueous phase is discarded, and the upper toluene phase is dried over 150 parts of anhydrous potassium carbonate overnight. The potassium carbonate is filtered off and the filtrate is then added slowly to a heated vacuum distillation set-up while toluene is continuously distilled off at a temperature of 25°-28° C. Nitrogen gas is continuously passed into the distillation column. After all the toluene is removed, the pressure is reduced to 0.1 mm Hg. 103 Parts of 2-(2-methoxyethyl)-2-imidazoline with a boiling point of 72°-84° C. and a melting point of 50°-51° C. are removed.

The 100 MHz 'H NMR spectrum of a CDCl$_3$ solution (~5) shows a single peak at 3.58$\delta$ due to ring —CH$_2$CH$_2$— hydrogens, a sharp single peak at 3.26$\delta$ due to the methoxy hydrogens and two triplets due to the chain —CH$_2$CH$_2$— hydrogens. The triplet belonging to the CH$_2$ adjacent to the methoxy group is located at 3.61$\delta$; the other CH$_2$ triplet is at 2.52$\delta$. This latter CH$_2$ and the ring —CH$_2$CH$_2$13 are slightly coupled to each other, so that one sees evidences of fine structure in those peaks under high resolution conditions.

The areas under each of the peaks correspond to the correct numbers of hydrogens

EXAMPLE 2

To a 3-necked, round-bottomed reaction vessel equipped with stirrer, thermometer, reflux condenser, addition funnel, nitrogen inlet and means for cooling, are added 350.0 parts of methylene chloride and 80.0 parts of methyl-3-methoxypropionimidate hydrochloride. The solution is cooled to −4° C. and a solution of 31.25 parts (equimolar amount) of ethylenediamine in 100 parts of methylene chloride are added at a rate such that the temperature remains between −4° C. and −8° C. The resultant solution is then stirred overnight and allowed to warm to room temperature. Stirring is continued, nitrogen gas is bubbled through the reaction media and the mixture is heated to reflux until ammonia evolution ceases. After filtration, washing and drying, 74.0 parts of waxy, crystalline material is obtained. Two recrystallizations, one from alcohol ether and one from 1,2-dichloroethane give a material having a melting point of 102°-104° C. identified as 2-(2-methoxyethyl)-2-imidazoline hydrochloride by IR spectrum and NMR. During the recrystallizations, ethylenediamine dihydrochloride is filtered off and identified.

The 100 MHz 'H NMR spectrum of a DMSO-d$_6$ solution (~5%) shows a sharp single peak at 3.81 $\delta$ due to the ring —CH$_2$CH$_2$— hydrogens, a sharp single peak at 3.26 $\delta$ due to the methoxy hydrogens, and two triplets due to the chain —CH$_2$CH$_2$— hydrogens. The triplet belonging to the CH$_2$ adjacent to the methoxy group is located at 3.68 $\delta$; the other CH$_2$ triplet is at 2.79 $\delta$. The areas under each of the peaks correspond to the correct numbers of hydrogens.

EXAMPLE 3

100 Parts of 6N sodium hydrochloride in a suitable reaction vessel are cooled to 5° C with an ice-water bath and 22.7 parts of the 2-(2-methoxyethyl)-2-imidazoline hydrochloride of Example 2 are added to the cold solution. An oil separates. The contents of the vessel are transferred to a separatory vessel and the aqueous phase is extracted four times with 30 parts of reagent grade tetrahydrofuran. The combined tetrahydrofuran extracts are dried over anhydrous potassium carbonate for 15 hours. The potassium carbonate is then filtered off and the tetrahydrofuran solution is distilled to yield 14.0 parts of 2-(2-methoxyethyl)-2-imidazoline.

EXAMPLES 4-17

Following the procedures of Example 1, Part A, various cyano compounds are reacted with various alcohols in the presence of various acids in accordance with Equations IA and IB, above. The charge materials used and the resultant products are set forth in Table I, below.

TABLE I

| | Charge According to Equations IA or IB | | | | |
|---|---|---|---|---|---|
| Example | Y | R' | R$^3$ | X | Product |
| 4 | C$_2$H$_5$O | H | C$_2$H$_5$ | Cl | Ethyl-3-ethoxypropionimidate hydrochloride |
| 5 | C$_4$H$_9$O | H | C$_4$H$_9$ | Br | n-butyl-3-n-butoxypropionimidate hydrobromide |
| 6 | C$_6$H$_{13}$O | CH$_3$ | C$_2$H$_4$OH | Br | 2-hydroxyethyl-3-(hexyloxy)-2-methylpropionimidate hydrobromide |
| 7 | C$_2$H$_5$O | H | CH$_3$ | Cl | Methyl-3-ethoxypropionimidate hydrochloride |
| 8 | C$_3$H$_7$O | H | 3-C$_4$H$_8$OH | Br | 3-hydroxybutyl-3-isopropoxypropionimidate hydrobromide |
| 9 | C$_{10}$H$_{21}$O | CH$_3$ | CH$_3$OCH$_2$ | F | Methoxymethyl-3-(decyloxy)-2-methylpropinimidate hydrofluoride |
| 10 | CH$_3$O | H | C$_2$H$_5$ | Cl | Ethyl-3-methoxypropionimidate hydrochloride |
| 11 | C$_{10}$H$_{21}$O | CH$_3$ | C$_2$H$_5$OC$_2$H$_4$ | I | 2-ethoxyethyl-3-(decyloxy)-2-methylpropionimidate hydriodide |
| 12 | — | H | C$_2$H$_5$ | Br | Ethyl lactimidate hydrobromide |
| 13 | OH | H | CH$_3$ | Cl | Methyl-2-methyllactimidate hydrochloride |
| 14 | OH | H | CH$_3$ | Cl | Methyl hydracrylimidate hydrochloride |
| 15 | — | C$_6$H$_5$ | C$_3$H$_7$ | F | Propyl-α-methylmandelimidate hydrofluoride |
| 16 | OH | CH$_3$ | i-C$_3$H$_7$ | Cl | Isopropyl-2-methylhydracrylimidate hydrochloride |
| 17 | OH | C$_6$H$_5$ | i-C$_3$H$_7$ | Cl | Isopropyl tropimidate hydrochloride |

EXAMPLES 18-32

Following the procedure of Example 1, Part B, the imidates of Examples 4-17 are converted to their corresponding imidazolines or tetrahydropryrimidines in accordance with Equations IIA, IIB, IIIA and IIIB, above. The results are set forth in Table II, below.

TABLE II

| Example | Imidate Of Example No. | R⁶ | Diamine R⁵ | R⁴ | n | Product |
|---|---|---|---|---|---|---|
| 18 | 4 | H | H | CH₃ | O | 2-(2-ethoxyethyl)-4(or 5)-methyl-2-imidazoline |
| 19 | 5 | H | C₆H₅ | H | O | 2-(2-butoxyethyl()-4(or 5)-phenyl-2-imidazoline |
| 20 | 6 | C₄H₉ | H | CH₃ | O | 1-butyl-2-[2-(hexyloxy)-1-methylethyl]-4(or 5)-methyl-2-imidazoline |
| 21 | 7 | H | H | C₂H₅ | 1 | 2-(2-ethoxyethyl)-4-ethyl-1,4,5,6-tetrahydropyrimidine |
| 22 | 8 | C₇H₇ | H | H | O | 2-(2-isopropoxyethyl)-1-O (m or p)-tolyl-2-imidazoline |
| 23 | 9 | H | CH₃ | CH₃ | O | 2-[2-decyloxy)-1-methyl-ethyl]-4,5-dimethyl-2-imidazoline |
| 24 | 10 | C₁₀H₉ | H | H | 1 | 2-(2-methoxyethyl)-1-[1 (or 2)-naphthyl]-1,4,5,6-tetrahydropyrimidine |
| 25 | 11 | H | C₇H₇ | H | O | 4 (or 5)-benzyl-2-[2-(decyloxy)-1-methylethyl]-2-imidazoline |
| 26 | 12 | H | H | H | O | α-methyl-2-imidizoline-2-methanol |
| 27 | 13 | H | H | H | O | α,α-dimethyl-2-imidazoline-2-methanol |
| 28 | 14 | H | H | H | O | 2-imidazoline-2-ethanol |
| 29 | 15 | H | H | H | O | α-methyl-α-phenyl-2-imidazoline-2-methanol |
| 30 | 15 | H | H | H | 1 | 1,4,5,6-tetrahydro-α-methyl-α-phenyl-2-pyrimidinemethanol |
| 31 | 16 | H | H | H | O | α-methyl-2-imidazoline-2-ethanol |
| 32 | 17 | H | H | H | 1 | 1,4,5,6-tetrahydro-α-phenyl-2-pyrimidineethanol |

EXAMPLES 33–41

Following the procedure of Example 2, various of the imidates of Examples 4–17 are converted to their corresponding imidazoline or tetrahydropyrimidine hydrohalides in accordance with Equations IVA and IVB, above. The results are set forth in Table III, below.

TABLE III

| Example | Imidate Of Example No. | R⁶ | Diamine R⁵ | R⁴ | n | Product |
|---|---|---|---|---|---|---|
| 33 | 4 | H | H | CH₃ | O | 2-(2-ethoxyethyl)-4 (or 5)-methyl-2-imidazoline hydrochloride |
| 34 | 6 | H | H | C₂H₅ | 1 | 4-ethyl-2-[2-(hexyloxy)-1-methylethyl]-1,4,5,6-tetrahydropyrimidine hydrochloride |
| 35 | 7 | H | C₆H₅ | H | O | 2-(2-ethoxyethyl)-4 (or 5)-phenyl-2-imidazoline hydrochloride |
| 36 | 9 | C₇H₇ | H | H | O | 1-benzyl-2-[2-(decyloxy)-1-methylethyl]-2-imidazoline hydrochloride |
| 37 | 10 | C₁₀H₇ | H | H | 1 | 1,4,5,6-tetrahydro-2-(2-methoxyethyl)-1-(1-naphthyl) pyrimidine hydrochloride |
| 38 | 11 | H | C₇H₇ | H | O | 2-[2-(decyloxy)-1-methylethyl]-4 (or 5)-p-tolyl-2-imidazoline hydrochloride |
| 39 | 12 | H | H | H | O | α-methyl-2-imidaxoline-2-methanol hydrochloride |
| 40 | 13 | H | H | H | 1 | 1,4,5,6-tetrahydro-α,α-dimethyl-2-pyrimidine hydrochloride |
| 41 | 15 | H | H | CH₃ | O | α,4 (or 5)-dimethyl-α-dimethyl-2-imidazoline-2-methanol hydrochloride |

EXAMPLES 42–50

The procedure of Example 3 is again followed except that the products of Examples 33–41 are used as charge materials. In each instance, the hydrohalides are converted to their corresponding imidazolines.

We claim:

1. A compound having the formula

wherein $Y$ is $R^2O$, $R^2$ being alkyl ($C_1$–$C_{10}$), aryl ($C_8$–$C_{10}$) or aralkyl ($C_7$–$C_{11}$), $R^1$ is hydrogen, methyl or phenyl and Q is

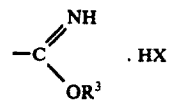

wherein $R^3$ is alkyl ($C_1$–$C_4$), hydroxyalkyl ($C_2$–$C_4$) or alkoxyalkyl ($C_2$–$C_4$) and X is a halogen.

2. A compound according to the claim 1 wherein Y is methoxy, $R^1$ is hydrogen, X is chlorine and $R^3$ is methyl.

3. A compound according to claim 1 wherein Y is ethoxy, $R^1$ is hydrogen, X is chlorine and $R^3$ is ethyl.

4. A compound according to claim 1 wherein Y is ethoxy.

5. A compound according to claim 1 wherein $R^3$ is ethyl.

6. A compound according to claim 1 wherein $R^1$ is methyl.

* * * * *